United States Patent [19]

Rho

[11] Patent Number: 6,086,541
[45] Date of Patent: Jul. 11, 2000

[54] METHOD FOR TESTING HEARING ABILITY BY USING ARS (AUTOMATIC VOICE RESPONSE SYSTEM) RUN BY A COMPUTER, A PROGRAM THEREFOR AND A NOISE BLOCKER

[76] Inventor: YunSung Rho, #603-1207 Jugong Apt. Block 6, Inchang-dong, Kuri-shi Kyunggido, Rep. of Korea

[21] Appl. No.: 09/285,351

[22] Filed: Apr. 2, 1999

[30] Foreign Application Priority Data

Dec. 22, 1998 [KR] Rep. of Korea ....................... 98-58698

[51] Int. Cl.$^7$ ....................................................... A61B 5/00
[52] U.S. Cl. ............................................. 600/559; 379/451
[58] Field of Search ............................... 600/559; 73/585; 181/138, 175, 198; 379/433, 451, 453

[56] References Cited

U.S. PATENT DOCUMENTS

| | | |
|---|---|---|
| 3,169,171 | 2/1965 | Waches et al. . |
| 3,808,354 | 4/1974 | Feezer . |
| 3,809,811 | 5/1974 | Delisle et al. . |
| 4,964,161 | 10/1990 | Trowbridge . |
| 5,012,513 | 4/1991 | Dale et al. . |
| 5,119,826 | 6/1992 | Baart de la Faille . |
| 5,928,160 | 7/1999 | Clark et al. ............................. 600/559 |

*Primary Examiner*—Max Hindenburg
*Attorney, Agent, or Firm*—Merchant & Gould P.C.

[57] ABSTRACT

The present invention is related to a method for making a remote diagnosis, a program therefor, and a noise blocker.

Conventionally, in order to test hearing ability or be diagnosed, it is necessary for a patient to visit a hospital, i.e., otorhinolaryngology section.

The present invention provides the program which enables the patient to receive the diagnosis without seeing a doctor, by ARS (automatic voice response system) that is run by a computer through a conventional telephone line.

In the present invention, if the patient calls, the ARS lets the patient hear audible frequency and sound volume, which are reference to the hearing ability every step according to the sequential information of the program. Then, the patient pushes the telephone button and informs the program of his hearing ability range. Based on the input range of the phone button, the program will notify the patient of his hearing ability through the voice message and, furthermore, explain the measures necessary for the hearing ability of the patient. According to the present invention, it is possible that the patient can receive the diagnosis easily.

3 Claims, 5 Drawing Sheets

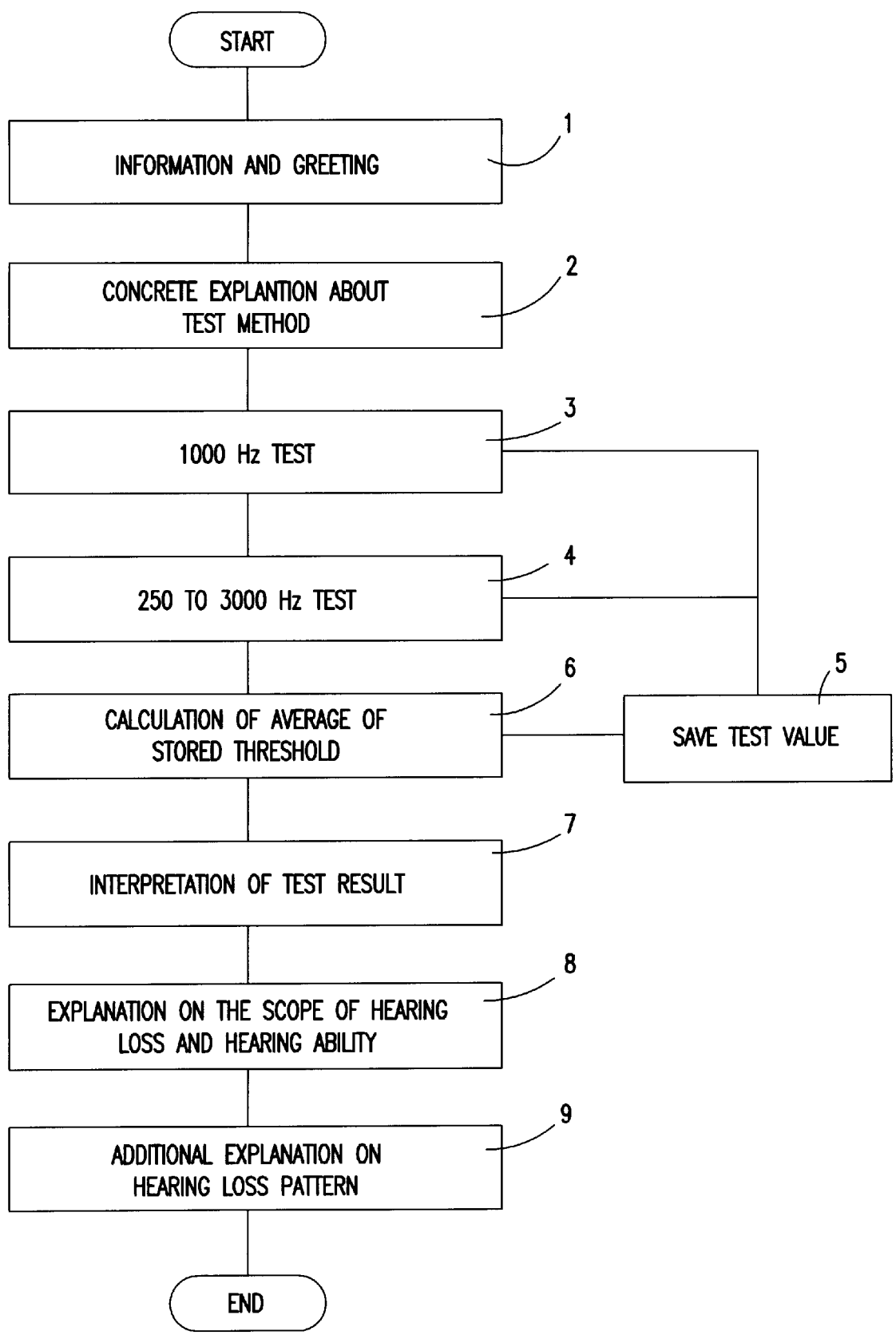

METHOD FOR TESTING HEARING ABILITY BY USING ARS (AUTOMATIC VOICE RESPONSE SYSTEM) RUN BY A COMPUTER, A PROGRAM THEREFOR AND A NOISE BLOCKER

BACKGROUND OF THE INVENTION

1. Field of Invention

The present invention is related to a computer program for testing hearing ability by using ARS telephone that is run by a computer, and a noise blocker.

2. Description of the Related Art

The hearing ability is one of important senses that a man has, and it contributes to information gathering together with the eyesight. Thus, the man should be aware of his hearing ability, specifically, how much he can hear.

However, such hearing ability gradually declines as a man becomes old. It is very usual phenomenon. Thus, it is likely that the man himself does not feel change in his hearing ability.

In particular, due to recent industrial development and rapid changes, the working condition is deteriorated.

In general, if a man works for a long time in a noisy environment, human body is accustomed to noises that occur around the working place. This causes the hearing ability to be weaken, and then, leads to hearing loss state. In addition, it is possible that drug addiction or an accident may cause the hearing disability to be accompanied.

Such a change in the hearing ability can be immediately treated or corrected if it is noticeable and, therefore, can be recognized in a short time. However, if the attenuation in the hearing ability proceeds very slowly, it is much likely that it cannot be recognized.

In this case, the patient needs to periodically visit the hospital by himself and test his hearing ability by the conventional hearing ability test machine. Otherwise, for self-test, it is necessary to prepare a tuning fork that can generate fiery pure sound and to test the hearing ability frequently. This enables the patient to know the change in his hearing ability.

However, such hearing diagnosis method has the following disadvantages: in case that it is needed to visit the hospital, inconveniences such a:, time loss, a need for reservation to see a doctor, etc., may occur. Also, in case of the self-test, there is a problem that special equipment for the self-test cost a patient too much.

SUMMARY OF THE INVENTION

The present invention is to provide a diagnosis method for resolving the above-mentioned conventional problems. According to the present invention, the patient can test his hearing ability any time without spending time on visiting the hospital and making the reservation. Also, according to the present invention, it is not necessary to buy the special equipment for the self-test. According to the present invention, it is possible for the patient to test his hearing ability any time and at any place.

According to the present invention, computer loads the program and runs the ARS by the loaded program. At the same time, it executes the test program for the hearing ability. Then, based on the sequential grades of the hearing ability, the hearing ability is tested and is automatically reported to a person who requests the test (hearinafter, "request person"). Then, the necessary measures and cautions based on the tested hearing ability are explained to a client. Based on the above, the object of the present invention is to provide a method for testing the hearing ability, in which a client can know his hearing ability very easily and quickly.

BRIEF EXPLANATIONS OF DRAWINGS

FIG. 1 shows a block diagram of the present invention.

DESCRIPTION OF THE PREFERRED EMBODIMENTS

Hereinafter are provided the detailed explanations of an example for the hearing ability test to accomplish the above-mentioned object of the present invention, referring to the attached drawings.

Figure 2A:
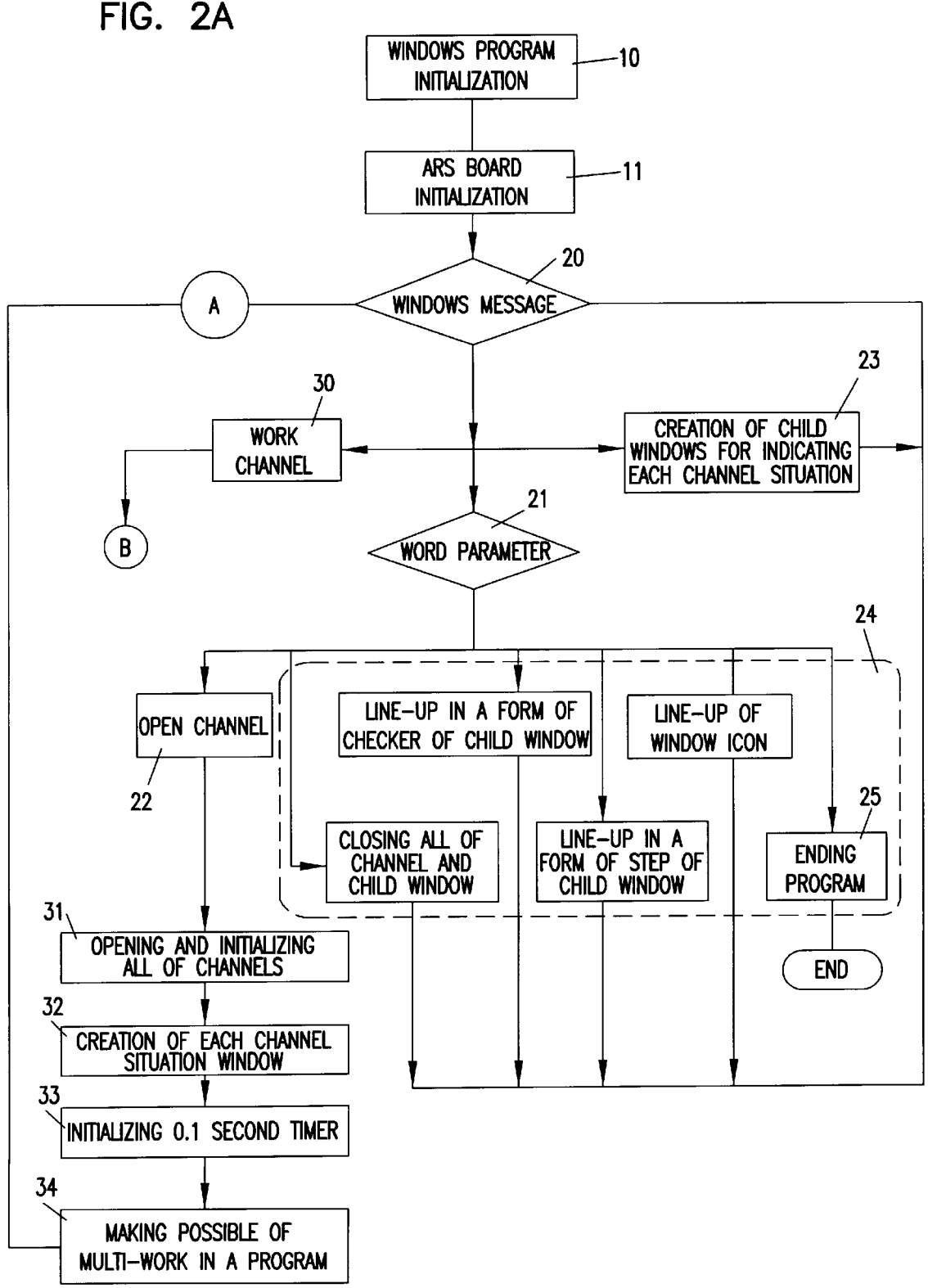
FIG. 2a and 2b show a flow chart of the present invention.
Figure 2B:
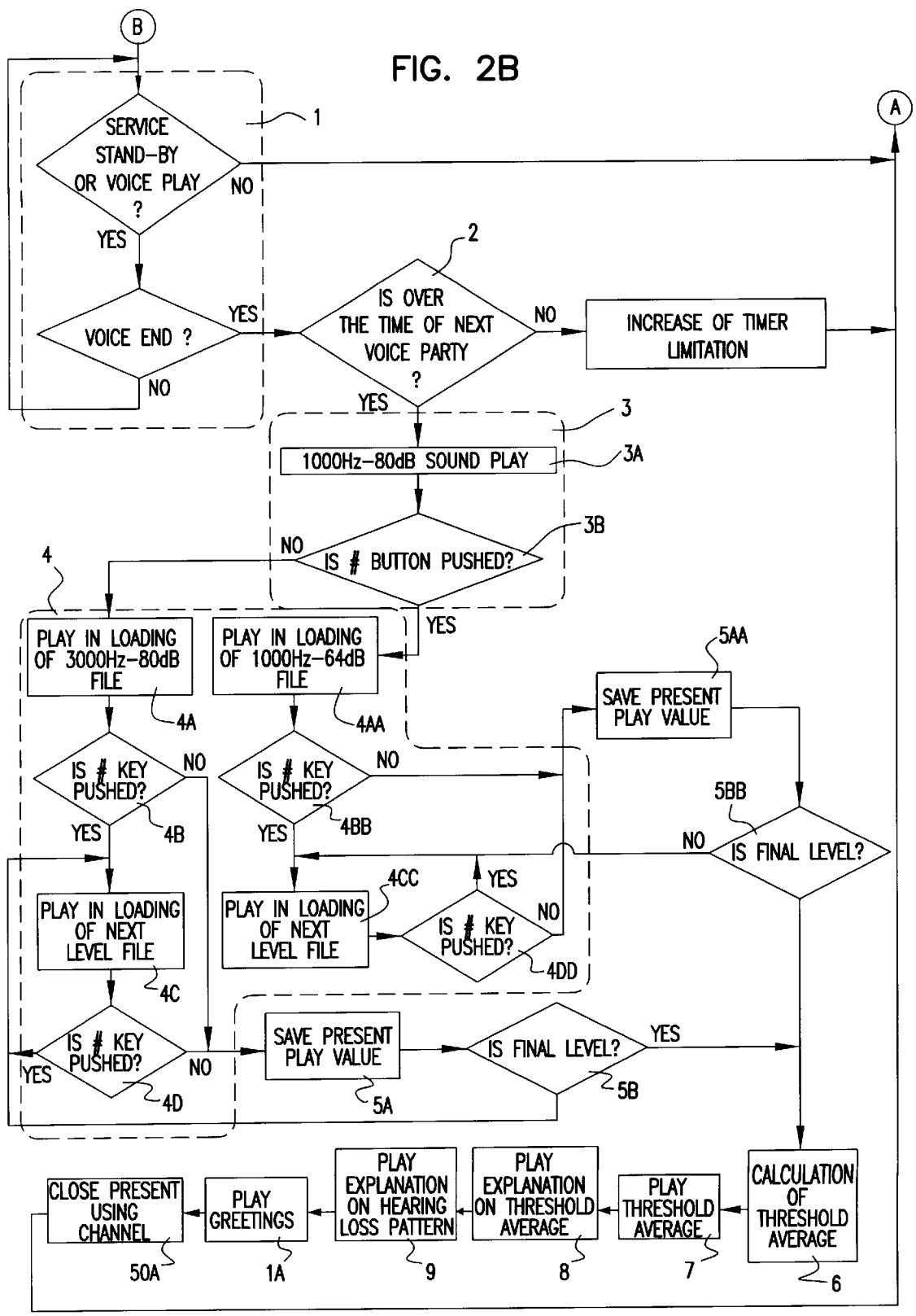
Figure 3:
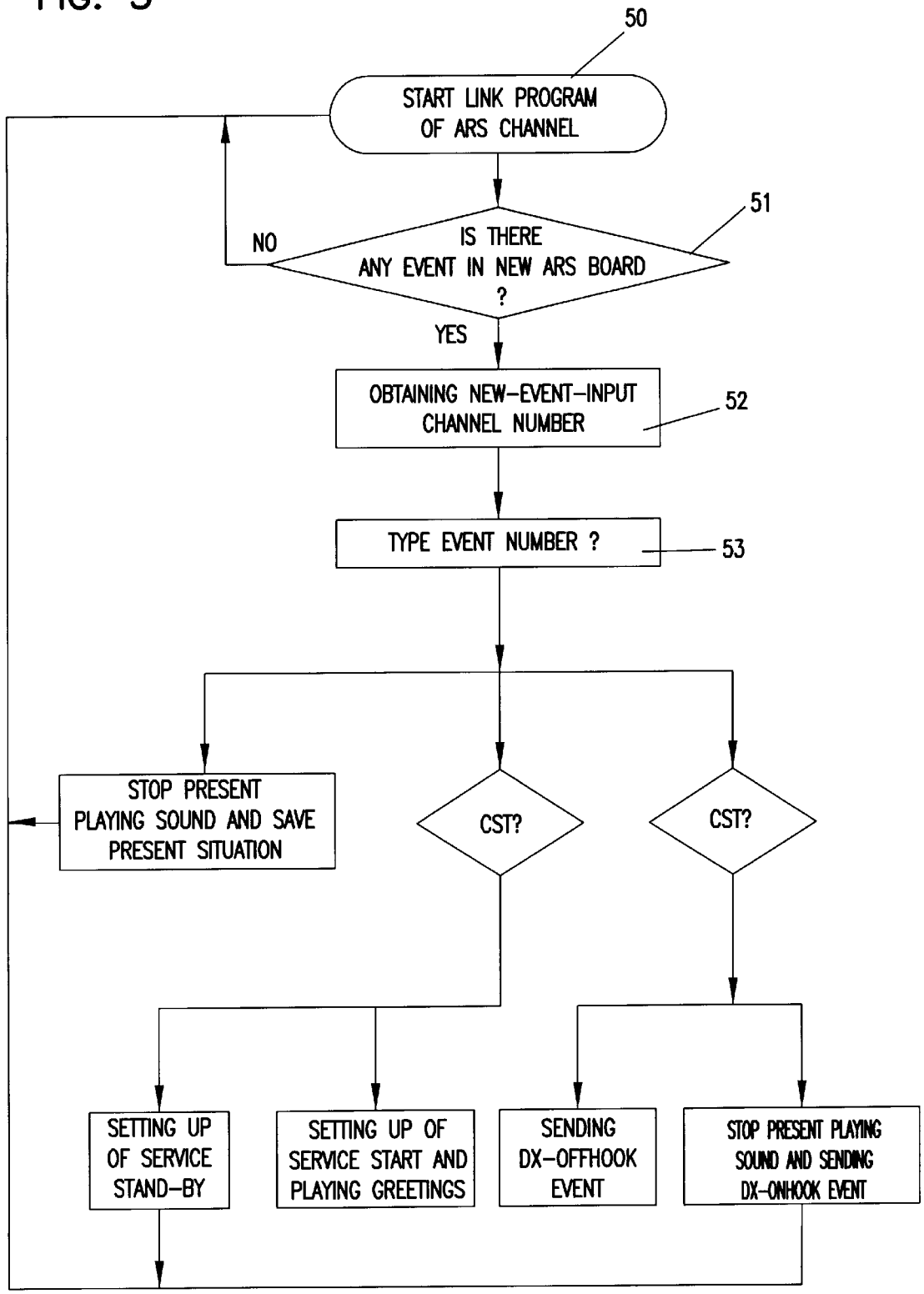
FIG. 3 shows a flow chart of ARS channel connecting program for the hearing ability test in accordance with the present invention.

FIG. 1 shows a block diagram, which briefly explains the program of the present invention. FIGS. 2a and 2b are a flow chart of the program in accordance with the present invention. The program is complied so that it can be loaded and executed by a computer. It is contained in an auxiliary storage device such as a hard disk ("HD"), a floppy disk ("FD") or CD-ROM.

The program in accordance with the present invention is divided into two parts, where one is a program for testing the hearing ability and the other is a ARS channel control program for connecting the test program with the telephone line.

First of all, if a client calls, the program for testing the hearing ability is logged-on after the ARS control program connects the telephone line with the empty ARS channel and clears the current channel.

The logged-on test program makes the voice message for information and greeting played in the introduction part (1) so that a client can hear it. Then, it executes a test explanation part (2) for explaining the test method. It makes a medium pitch test part (3) operate so that it calculates and determines a starting point of the hearing ability test. The test part (3) has 1000 Hz frequency range, which is a medium test value between 250 Hz and 3000 Hz frequency range. The test program makes a detailed test part (4) execute. The detailed test part (4) has frequency grades which are 250, 500, 1000, 1500, 2000 and 3000 Hz between 250 Hz and 3000 Hz. It has sound volume, which is divided equally by 13 between 0 dB and 60 dB at the frequency of 250 Hz, by 15 between 0 dB and 70 dB at the frequency of 500 Hz, and by 17 between 0 dB and 80 dB at each frequency of 1000, 1500, 2000 and 3000 Hz. The detailed test part (4) plays the above sound from high pitch to low pitch in a predetermined interval.

The detailed test part (4) checks a telephone button input in response to sound played in each frequency range, recognizes the sound volume of the telephone button pushed last in each frequency range, and stores it into a test threshold value storage part (5).

Next, a threshold value calculating part (6) fetches a stored value from the test threshold value storage part (5). It calculates an average value by using arithmetic mean method at the frequency 500, 1000 and 2000 Hz (significant frequency in the hearing ability test). The average value is sent to an interpretation part (7). An explanation part for interpreted value (8) fetches explanation voice for hearing loss range corresponding to the average value and completes playing the voice. An additional explanation part (9) plays an additional explanation voice for hearing loss pattern, further detailed explanation and necessary measures.

The above-mentioned operations for testing the hearing ability according to the present invention are explained in further detail below, referring to FIGS. 2a and 2b.

The present invention is compiled program which is run under the operation of the operating system. The ARS Board (automatic response voice system) is installed in an expanded slot which exist in a main board of a computer or outer packing type device.

The example of the present invention is programmed to run under the "Windows" of the Microsoft, Inc., the program is written in "Visual C++," voice edition is using "Cool editor 96" and ARS Board is "Dialogic."

The sound, "1000 Hz–30 dB" is stored from the hearing ability test device into voice recognition device, and is compressed and amplified, so that 0 dB~60 dB is divided equally by 13 at each frequency of 250 Hz, 0 dB~70 dB by 15 at the frequency of 500 Hz, 0 dB~80 dB by 17, at each frequency 1000, 1500, 2000, 3000 Hz. These are divided into individual files that are encoded in a predetermined voice data type and exist in the storage device that contains the present program under the operating system.

And, by executing the main execution file, i.e., the hearing ability test program through linking with the ARS control program, the two programs are programmed to supplement each other by providing On-Hook setting value, Off-Hook setting value and channel value of a client to a main program.

For reference, the term, "pure sound," which is one of terms described in the present invention, means that the sound has pure and inherent waveform with adding no other waveforms which function as noises thereto. The term, "threshold," is a minimum sound intensity (volume) in which transmitted sound can be recognized by stimulating eardrum. The term, "child window" is a subordinate message window which can be created and be open when the program is executed by the parameter under the Windows operating system. The term, "event" means the state in which the telephone is connected by a client.

Herein below are explained operations of the present invention.

As shown in FIGS. 2a and 2b, while the computer is operating by running the window operating system (10), a hardware controller (11) initializes the ARS Board and prepares its operation. Based on the automatically executed instructions of the window system, the hearing ability test program is executed and an active window (20), which displays the window message on wallpaper, is created.

The hearing ability test program executed as mentioned above drives work channel (30) (which manages the ARS board), word parameter (21) and child window generator (23).

At this time, the word parameter (21) drives window arrangement part (24) so that the child window is arranged in a checker board pattern, arid window icons are arranged on the wallpaper, in order to make the screen as clear as possible. This is executed by the typical function in which the Windows operating system has. The program is intended to have a function of screen arrangement only.

And, there is a program close selection part (25) in the one side of the active window (20).

Meanwhile, open channel (23) drives and a channel initialization part (31) for opening and initializing telephone line connected to the ARS board is displayed by the child window generator (32). Then, the timer (33) goes round and checks each channel.

As mentioned above, to open each checked channel simultaneously or to control each channel separately, the multi-tasking set (34) recognizes and holds the data. The data obtained by this execution is provided to the active window (20).

At that time, the ARS channel connection program (50) activates a searching program (51) to check on-hook state. If a client who wants the hearing test calls, new events is generated and allocated to an empty channel. The channel number is intercepted by a number obtainer (52). A connection number provider (53) provides a number to each connection event and the event number to the child window generator (23). Thus, the hearing test is started.

If the events happen as mentioned above, the introduction part (1) along with the work channel (30) is activated and plays voice message for an information and greeting (attached FIG. 2b).

The information and greeting is "Hello. This program is the hearing test by using the phone."

After this voice message is played and the time during which the message is being played is counted, the test explanation part (2) runs the following voice message. "Please listen to this message with one ear that has better hearing ability than the other as possible.

If possible, please use the telephone with high sensitivity and take the test at the quiet surroundings with little noise. By doing so, you will get a more accurate result.

Please listen carefully to the detailed explanations regarding the level of your hearing ability, which will be presented right after the test.

We will start the test from now on.

Please take the receiver near the ear that you want to Lest. Please press "#" button within five seconds if you hear the beep sound, even though it is very weak. If you can't hear the beep sound and don't press the button within five seconds, it will go on to the next step of the test.

We will explain again.

Please press "#" button if you hear the beep sound, even though it is very weak. If you can't hear any sound, please stay calm. Then, the test will be continued until it is ended.

In a few seconds, the test will be started."

If the test explanation part (2) proceeds as described above, the medium pitch test part (3) operates. It plays "beep" sound whose frequency is 1000 Hz and sound volume is 80 dB for one second in a medium pitch generating part (3A). Then, it checks whether the "#" button among other phone buttons is pressed or not. Based on this, a medium pitch conversion part (3B) determines the starting value for the test.

In the above step, unless "#" button is pushed, the program recognizes that a client cannot hear the medium pitch, i.e., "1000 Hz–80 dB." Thus, the program operates so that the test begins from the highest pitch, "3000 Hz–80 dB," which is applicable to the patient who suffers from the hearing loss, by generating the sound in a maximum pitch generator (4a) of the detailed test part (4).

If the "#" button is pushed, the program makes the medium pitch generating part (4aa) operate.

The setting of the medium value as mentioned above makes it possible to avoid unnecessary test for upper grades because most of clients have the hearing ability whose level is capable of hearing telephone conversation.

When the medium pitch test part (3) determines the ongoing point and the detailed test part (4) proceed, the sound of "3000 Hz–80 dB" grade is played in the maximum pitch generating part (4a). Then, after it is checked whether the "#" button is input in a button input part I (4b), the next grade sound, i.e., "3000 Hz–64 dB" is played in the grade conversion part (4c) for one second. Unless the "#" button is pushed in the button input part I (4b), the grade sound of "3000 Hz–80 dB," which was played before, is stored in the test threshold value storage part (5a).

As mentioned above, if the next grade sound is played in the grade conversion part (4c), the button input part II (4d), which confirms the response of a client, checks the "#" button input. If there is the input, it is returned again to the grade conversion part (4c). Then, low pitch of the next grade, "3000 Hz–48 dB," is played for one second, and checks again the "#" button input of a client in the button input part II (4d).

As mentioned above, the test continues until the sound volume of "3000 Hz" frequency band is tested up to "0 dB" level. At this time, if a client cannot hear a certain sound volume in the "3000 Hz" frequency band, he/she will not push the "#" button.

Unless a client pushes the "#" button, the button input part II (4d) stores the sound value that was played immediately before in the test threshold value storage part (5a).

Next, the current sound grade is compared with the sound whose frequency is "250 Hz" and the sound volume is "0 dB" (which is set as the lowest grade) in the sound grade ending part (5b).

At this time, the above-explained sound volume for "3000 Hz" frequency band is returned again to the grade conversion part (4c). This is, because much lower frequency band remain. Thus, the next frequency band, "2000 Hz–80 dB," is played for one second.

Finally, a client is made to hear up to the final grade sound for the low sound grades. The threshold value which a client has heard stored in the test threshold value storage part (5a).

In addition, in case that the medium pitch generating part (4aa) proceeds by means of the medium value test part (3) as mentioned above, the hearing ability of a client corresponds to the level where he can hear the "1000 Hz" frequency and "80 dB" sound volume. Therefore, by starting the test from the sound grade below the above level, it is possible to reduce the unnecessary time loss which is caused by playing the sound below the medium grade. The progress herein below is programmed as described above.

In other words, the sound having the "1000 Hz–80 dB" grade is played in the medium pitch generating part (4aa) for one second and a client's "#" button input in response to the sound is checked in the button input part Ia (4bb). Then, the threshold value is stored in the test threshold value storage part (5aa) or the, next grade proceeds in the grade conversion part (4cc). Subsequently, a sound close, part (5bb) determines whether last sound grade is played or not, and, as a result, that makes every sound grade played.

As explained above, the threshold grades of a client in response to each sound grade are stored in the test threshold value storage part (5aa) or test threshold value storage part (5bb).

Subsequently, the threshold grades of a client, which are stored in the test threshold value storage part (5aa, 5bb), are fetched into a threshold value calculation part (6) and average of the stored threshold value is calculated.

A client can hear voice corresponding to the calculated average threshold average value by means of the interpretation part (7). At this time, the voice is amplified to enable a client to hear easily.

Such played voice is as indicated in "Table 1."

TABLE 1

| Threshold Average Value | Played Voice |
|---|---|
| 0 dB | Threshold of hearing ability for tested one ear is 0 dB |
| 5 dB | Threshold of hearing ability for tested one ear is 5 dB |
| 10 dB | Threshold of hearing ability for tested one ear is 10 dB |
| 15 dB | Threshold of hearing ability for tested one ear is 15 dB |
| 20 dB | Threshold of hearing ability for tested one ear is 20 dB |
| 25 dB | Threshold of hearing ability for tested one ear is 25 dB |
| . . . | |
| 85 dB | Threshold of hearing ability for tested one ear is 85 dB |

After the voice corresponding to the threshold average value is played as above, the threshold average values are divided into five categories. Voice for explanation corresponding to one of them is played in the interpreted value explanation part (9), so as to explain the meaning of the test threshold value to a client.

The voice message played in the above-mentioned interpreted value explanation part (9) is as indicated in "Table 2."

TABLE 2

| Interpreted value range | Played Voice |
|---|---|
| 0 dB–25 dB | Hearing ability of a tested ear is normal. |
| 26 dB–40 dB | A tested ear suffers from mild hearing loss. There is no difficulty in the daily conversation. However, it is expected that it may be difficult to hear weak or whispering sound. If your hearing ability declines within a month and a singing in the ear or dizziness is accompanied, please consult to a doctor whose specialty is otorhinolaryngology as soon as possible. If you have pus from the ear or you continue to feel that the ear is filled with pus, there is possibility of "otitis media." Therefore, please consult to the doctor. |
| 41 dB–55 dB | A tested ear suffers from moderate hearing loss. There is difficulty in the daily conversation. It is required to receive early treatment and it is helpful to wear a hearing aid. If your hearing ability is declined within a month or a singing in the ear or dizziness is accompanied, please consult to a doctor whose specialty is otorhinolaryngology as soon as possible. If you have pus from the ear or you continue to feel that the ear is filled with pus, there is possibility of "otitis media." Therefore, please consult to the doctor. |
| 56 dB–70 dB | A tested ear suffers from moderately severe hearing loss. It is expected that you may have conversation with others almost only with loud voice and you cannot hear others clearly. It is necessary to wear a hearing aid because of severe difficulty in the daily conversation. If your hearing ability declines within a month or a singing in the ear or dizziness is accompanied, please consult to a doctor whose specialty is otorhinolaryngology. If you have pus from the ear or you feel that the ear is filled with the pus, there is possibility of "otitis media." Therefore, please consult to the doctor. |
| 71 dB–80 dB | A tested ear suffers from severe hearing loss. Even if loud voice is spoken close to your ear, you hardly hear the sound. It is impossible to have the daily conversation and, therefore, is required to wear a hearing aid |

As mentioned above, the interpreted value explanation part (8) calculates which range the threshold average value [which is obtained from the threshold value calculation part (6)] corresponds to, and plays explanation for the corresponding interpreted value range as voice.

Subsequently, the program computes the hearing loss pattern by calculating the degree of distribution for hearing ability threshold value. Then the program explains the additional explanation as indicated in "Table 3" according to the computed value.

TABLE 3

| Hearing Loss Pattern | Voice Message for Additional Explanation |
|---|---|
| P1 | The loss of hearing ability is found in the relatively high pitch range. Thus, it is possible not to hear low pitch sound. Also, it is expected that you keep on saying "I beg your pardon?" because you cannot hear clearly. |
| P2 | The loss of hearing ability is found in the relatively low pitch range. Thus, it is likely to have difficulty in the daily conversation |
| P3 | The loss of hearing ability is found in the conversation range. Thus, it is likely not to hear a daily conversation clearly when you talk with several people at the same time or when you talk at the noisy place. |
| P4 | The hearing ability is maintained in the conversation range but it is more decreased in the high and low pitch range. Thus, it is likely not to hear low pitch sound or not to hear a daily conversation clearly when you talk with several people at the same time or when you talk at the noisy place. |

When the additional explanation is finished, the following information is played by the test close information part (1a); "Thank you for calling. If you want more detailed counseling or have questions about hearing aid, call (0346) 573-2498. Thank you."

After the finishing information is played, the channel close part (50a) finishes the hearing ability test by disconnecting the telephone line connected to the ARS and making currently using channel off-hook state.

Figure 4:
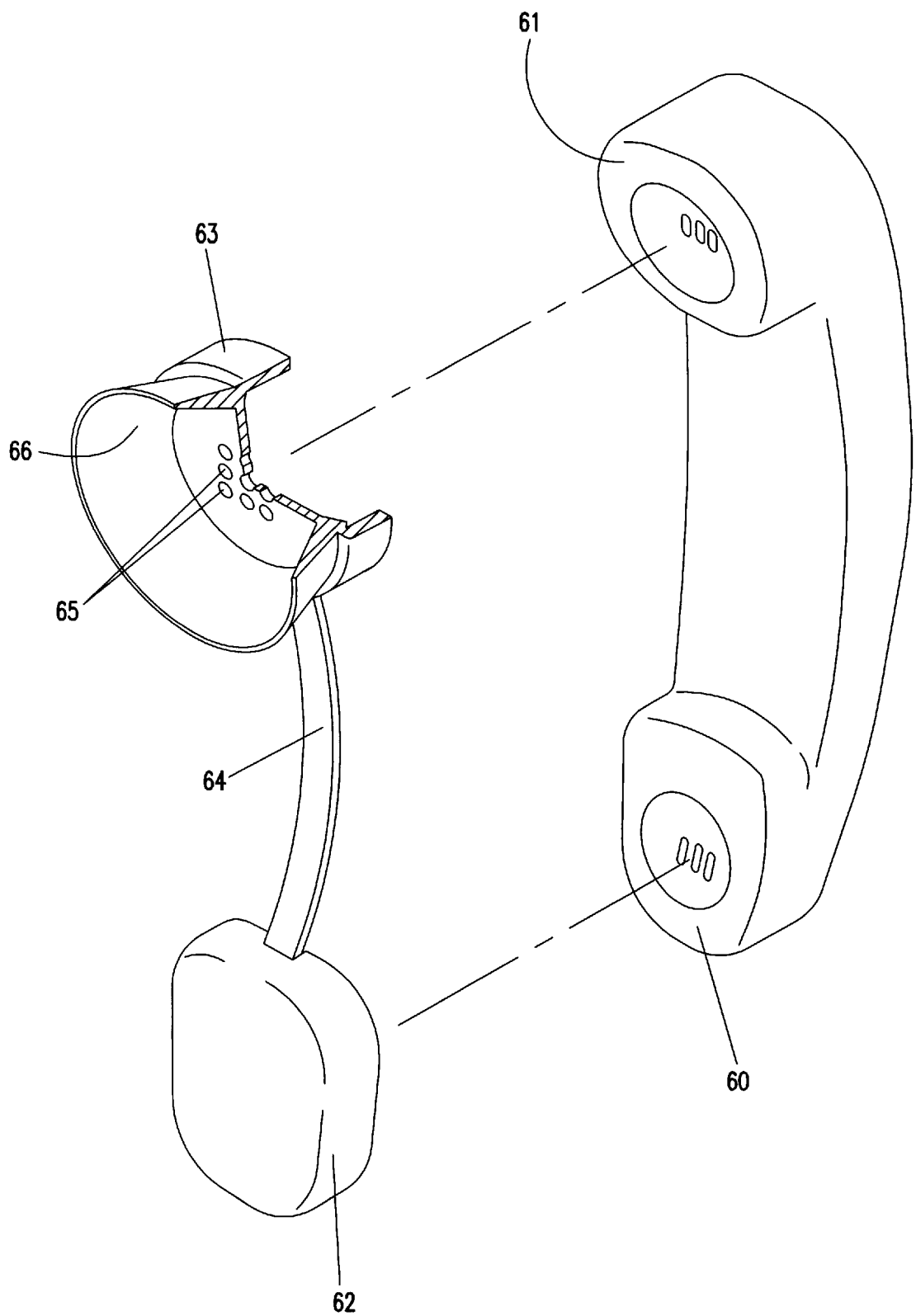
FIG. 4 shows a noise blocker, which is used for the hearing ability test in accordance with the present invention.

Meanwhile, in the hearing ability test according to the present invention, it is preferable to employ a device for blocking bone conduction and surrounding noises. As shown in FIG. 4, a noise blocker for blocking a transmitter and bone conduction of a receiver is used.

The blocker is made of very soft synthetic rubber and wraps the transmitter (60) and the receiver (61) with shape of cap. The transmitter cap (62) and the receiver cap (63) are formed integrally with each other through a connection part (64). The transmitter cap (62) is sealed. A plurality of holes are formed in the middle of the receiver cap (63). A contact part (66), which has trumpet shape, is formed outside the receiver cap (63), thereby preventing noise from entering into the receiver. The contact part (66) is made of flexible material to contact the head closely along its shape. Therefore, it is possible to block the bone conduction of sound and to provide the best test condition.

The hearing ability test program according to the present invention facilitates a request person to test his hearing ability frequently without visiting the hospital.

What is claimed is:

1. A method for testing hearing ability by using ARS run by a computer, comprising the steps of:

connecting calling of a person who requests the hearing ability test with a telephone line of the ARS run by the computer;

making the person hear corresponding sound volume for audible frequency range divided into multiple grades, each of which is a reference to the hearing ability test;

recognizing and checking a tone button input by the person in response to the sound volume;

computing a threshold value for the hearing ability of the person; and, informing the person of the hearing ability corresponding to the threshold value through voice message.

2. A medium containing hearing ability test program using ARS run by a computer, the program comprising:

an introduction part (1) and a test explanation part (2) which play information and greeting regarding the hearing ability test;

a medium pitch test part (3) which sets a starting point of the hearing ability test by playing sound, whose volume is 80 dB and frequency is 1000 Hz, and whose grade is a medium between 250 Hz and 3000 Hz range;

a detailed test part (4) having audible frequency grades, 250 Hz, 500 Hz, 1000 Hz, 2000 Hz and 3000 Hz between 250 Hz and 3000 Hz, and for playing stored grade sound from high pitch grade to low pitch grade in a predetermined interval, wherein the stored grade sound is to store sound volume, each of which is to divide 0 dB~60 dB equally into 13 at frequency 250 Hz, to divide 0 dB~70 dB equally into 15 at frequency 500 Hz, and to divide 0 dB~80 dB equally by 17 and at each frequency of 1000, 1500, 2000, and 3000 Hz;

a test threshold value storage part (5) for storing a threshold value for a predetermined grade by checking a button input by a person who requests the hearing test in response to each grade in the detailed test part (4);

a threshold value calculating part (6) for calculating an average value by fetching the stored value from the test threshold value storage part (5);

an interpretation part (7) for playing the average threshold value;

an interpreted value explanation part (8) for playing explanation voice for hearing loss range corresponding to the average threshold value; and, an additional explanation part (9) for making an additional explanation according to hearing loss pattern of the tested person.

3. A noise blocker for hearing ability test, wherein the blocker wraps a receiver (61) and a transmitter (60) of a telephone used in the hearing ability test with shape of cap, and a transmitter cap (62) and a receiver cap (63) are formed integrally with each other by a connection part (64); and, wherein the transmitter cap (62) is sealed for blocking the noises, arid a plurality of holes (65) are formed in the middle of the receiver cap (63) and a contact part (66) having trumpet shape is formed outside the receiver cap (63) for blocking bone conduction.

* * * * *